United States Patent [19]

Wallace

[11] Patent Number: Plant 6,674

[45] Date of Patent: Mar. 14, 1989

[54] HERITAGE CHESTNUT

[76] Inventor: Robert D. Wallace, Rte. 1, Box 341, Alachua, Fla. 32615

[21] Appl. No.: 37,946

[22] Filed: Apr. 13, 1987

[51] Int. Cl.[4] ..... A01H 5/00

[52] U.S. Cl. ..... Plt./30

[58] Field of Search ..... Plt./30

*Primary Examiner*—James R. Feyrer

[57] ABSTRACT

A tall, vigorous hybrid chestnut tree with very American chestnut-like characteristics, having a single, timber-form, upright, straight bole and a narrow branching habit, with large, elliptical and deeply dentate leaves and strongly scented flowers appearing in late spring after leafing out; the tree being a regular and light bearer of medium-sized, elongated, sweet nuts, the burrs splitting and many of the nuts falling free from the burr; the tree also exhibiting a high genetic resistance to the chestnut bark blight (*Endothia parasitica*), being a member of a group of hybrid chestnut trees that have not shown a single instance of infection in over 30 years of breeding and research, including passing inoculation tests without dying from infection, and the present variety itself not showing any instance of blight infection in 25 years of growth in the orchard.

1 Drawing Sheet

ORIGIN OF THE VARIETY

The present variety is a seedling American × Chinese hybrid chestnut, specially selected, growing in the Chestnut Hill Nursery orchards in Alachua, Fla. It was bred from hybrid chestnut trees (unpatented) produced from a cross made by my grandfather, Dr. Robert T. Dunstan. Flowering grafts of a native American chestnut (unpatented), found growing uninfected in a grove of dead and dying chestnuts, were crossed with a composite tree of 3 USDA released varieties of Chinese chestnut, Kuling, Meiling, and Nanking (all unpatented), in 1953 in North Carolina. Seedlings from this first cross were then backcrossed to the American parent tree. The resulting second generation was set out in the orchard where it exists today in excellent health. The present variety is a second generation seedling tree, exhibiting the most American chestnut-like characterisitcs and blight resistance that I have determined to be novel and distinct.

ASEXUAL REPRODUCTION OF THE VARIETY

Upon recognition of the outstanding characteristics of the present variety, it was asexually reproduced by myself by grafting onto Chinese chestnut rootstocks (unpatented). In maturity, all such reproductions run true to the original tree in all respects.

SUMMARY OF THE VARIETY

The present variety of hybrid chestnut tree is of large size, vigorous in growth, with the characteristic upright, straight-boled, timber-type growth form and narrow branching habit of the original American chestnut, having long, narrow, elliptical leaves with a deeply dentate margin, flowering in late spring after leafing out; the tree bearing regularly every year, and being a light bearer of medium-sized, elongated dark brown nuts with pointed stylar tips, 2–3 per burr, the nuts ripening in late September and early October, and the burrs cracking open as they ripen on the tree and many of the nuts falling free from the burr. The nuts are larger than but shaped like those of the American chestnut. The pellicle is thin and easily removed from the kernel, and the meat is cream colored and has the sweet, excellent taste of the American parent.

The present variety is characterized by being very similar to the original American chestnut, in tree form, foliage, nut shape and taste. It is distinguished from the Revival Chestnut (U.S. Plant Pat. No. 5,537), which was bred from the same line of hybrid chestnuts, by its more upright growth form, its elliptical and deeply dentate leaves, and its much more American-like, elongated nut. The present variety is cold hardy, yet able to grow well and bear as far south as north Florida. The trees are excellent for timber and woodlot nut production, for reforestation and landscaping.

The present variety is also importantly characterized by having never had any instance of blight infection or death from *Endothia parasitica* (the bark fungus that destroyed the entire chestnut population of the United States) in over 25 years of growth and observation in the Chestnut Hill Nursery orchards, even though there is blight found in the area surrounding the orchards. No American chestnuts have ever survived the blight without infection and very few adult trees are left living anywhere. The present variety has maintained the blight resistance of the Chinese chestnut in combination with the phenotypic characteristics of the American chestnut as a result of the crossing of the original first generation of hybrid seedlings back to the American parent tree.

BRIEF DESCRIPTION OF THE DRAWING

The drawing is an illustration, by photographic reproduction in color, of a twig with leaves and burrs and nuts out of the burrs.

DESCRIPTION OF THE VARIETY

The botanical details of this new and distinct variety of chestnut tree-with color definitions (except those in common color terms) referenced to *Maerz and Paul Dictionary of Color* — are as follows:

Tree:

*Size (at maturity).*—Large.

*Vigor.*—Vigorous.

Trunk:

*Form.*—Upright, straight-boled timber type.
*Texture.*—Smooth becoming rougher on older wood.
*Color of bark.*—Gray (12-A-1).

Branches:
*Form.*—Light.
*Texture.*—Smooth, glabrous on the twigs.
*Lenticels.*—Few, small.
*Branching habit.*—Narrowly spreading.
*Color.*—New wood: Gray brown (13-H-3). Mature wood: Gray (13-A-1).

Foliage:
*Quantity.*—Medium.
*Density.*—Medium.

Leaves:
*Size.*—Large. Average length — 7–9" (including petiole). Average width — 2".
*Shape.*—Elliptical with acute tip and base.
*Thickness.*—Medium.
*Texture.*—Glabrous.
*Margin.*—Deeply dentate.
*Petiole.*—Length: Medium. Thickness: Medium.
*Color.*—Top side — Glossy dark green (23-A-12). Under side — Lighter green (21-F-9).

Bloom:
*Amount of bloom.*—Medium.
*Color.*—Yellow white (17-C-1).
*Blooming period.*—Late. After leaf out in early May.
*Age at which tree starts flowering.*—3–4 years after graft placement.

Crop:
*Bearing.*—Regular (yearly) bearer.
*Productivity.*—Light.
*Ripening period.*—Short. September 25–October 5.
*Distribution of nuts on tree.*—Upper regions of the tree.
*Tenacity.*—Most of the crop released from the burrs.

Hull:
*Description.*—Rounded burr with elongated spines.
*Size.*—3–4" in diameter.

*Number of nuts.*—2–3 per burr.
*Dehiscence.*—Splits while still on tree.
*Color.*—Brown (15-A-12).

Nut:
*Size.*—Medium. Average size — 1"×$\frac{3}{4}$" thick. Average weight — 45–47.5 nuts per pound.
*Form.*—Rounded on the side, flat on other side.
*Blossom end.*—Elongated, with a hairy pointed tip.
*Basal end.*—Flattened.
*Color.*—Dark Brown (8-L-6).
*Shell.*—Thin.
*Hardiness of shell.*—Firm.
*Texture of shell.*—Smooth.
*Percentage of kernel to nut.*—Very high (95%).

Kernel:
*Size.*—Almost as large as nut size.
*Form.*—Same as nut shape.
*Pellicle.*—Thin, easily removed.
*Flavor.*—Very sweet.
*Color.*—Cream (10-D-1).

Resistance to insects: No unusual susceptibilities noted.
Resistance to disease: Very high inherent resistance to chestnut bark fungus (*Endothia parasitica*), no other susceptibilities to any other disease.

The chestnut tree and its nuts herein described may vary in slight detail due to climatic and soil conditions under which the variety may be grown; the present description being of the variety as grown in Alachua, Fla.

I claim:

1. A new and distinct variety of hybrid chestnut tree, substantially as illustrated and described, which is of large size, vigorous, upright, straight-boled, timber type form with large, elliptical leaves with deeply dentate margins and late (post leaf appearance) flowering; the tree being a light, regular bearer of medium sized, elongated, sweet nuts in burrs that crack in late September and early October and release the crop easily; the trees being especially characterized by resembling the American chestnut in tree form, foliage and nut quality and a high genetic resistance to the chestnut bark blight.

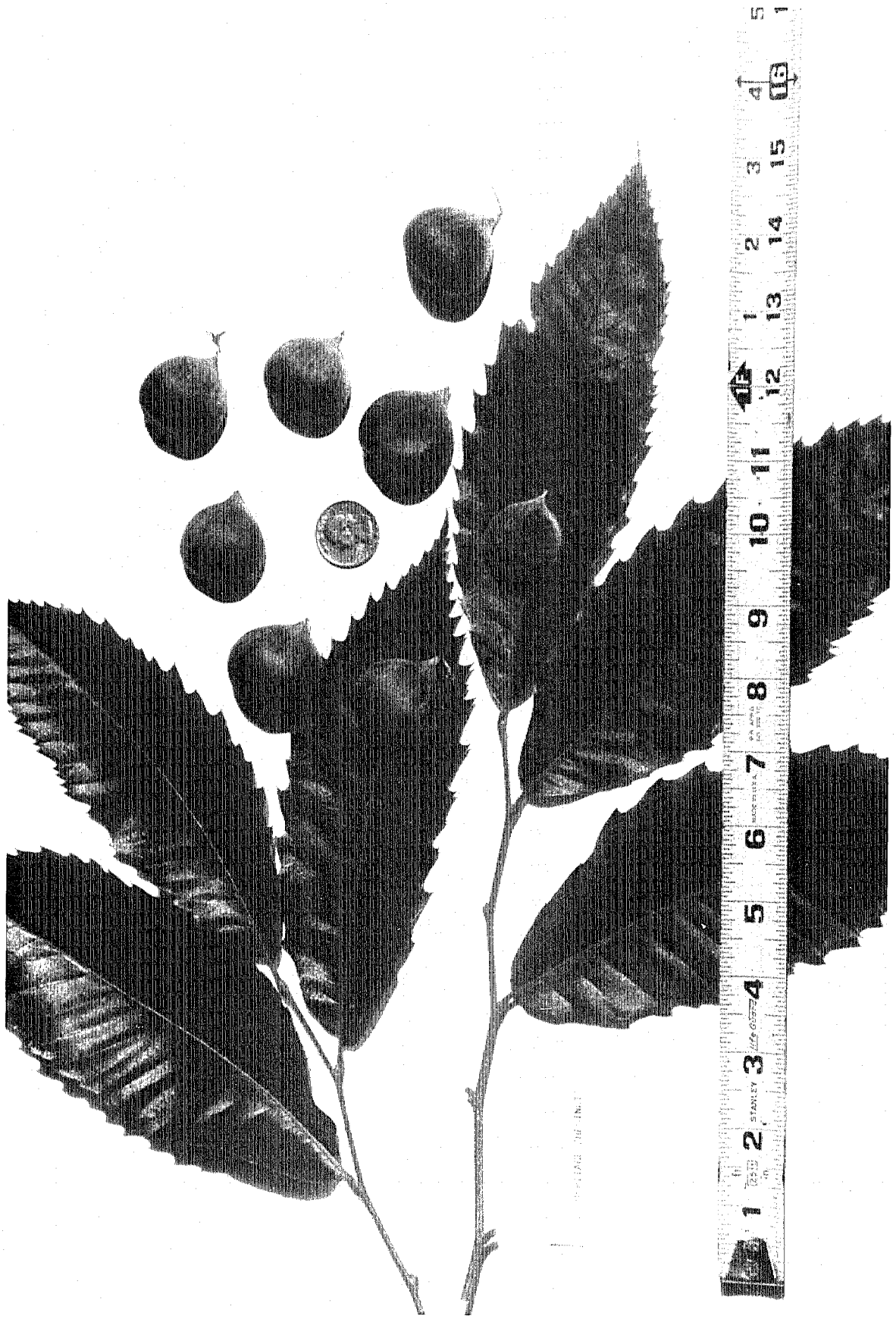

* * * * *